US009398916B2

(12) United States Patent
Mialhe

(10) Patent No.: US 9,398,916 B2
(45) Date of Patent: Jul. 26, 2016

(54) DEVICE FOR PLACING A VASCULAR IMPLANT

(76) Inventor: Claude Mialhe, Drauguignan (FR)

(*) Notice: Subject to any disclaimer, the term of this patent is extended or adjusted under 35 U.S.C. 154(b) by 1471 days.

(21) Appl. No.: 10/553,007

(22) PCT Filed: Mar. 22, 2004

(86) PCT No.: PCT/FR2004/050118
§ 371 (c)(1),
(2), (4) Date: Aug. 7, 2006

(87) PCT Pub. No.: WO2004/091410
PCT Pub. Date: Oct. 28, 2004

(65) Prior Publication Data
US 2007/0078504 A1    Apr. 5, 2007

(30) Foreign Application Priority Data

Apr. 10, 2003  (FR) ...................................... 03 50096

(51) Int. Cl.
*A61M 29/00*   (2006.01)
*A61F 2/06*    (2013.01)
(Continued)

(52) U.S. Cl.
CPC ....... *A61B 17/12109* (2013.01); *A61B 17/0057* (2013.01); *A61B 17/12172* (2013.01); *A61B 17/3439* (2013.01); *A61F 2/95* (2013.01); *A61F 2/962* (2013.01); *A61F 2/966* (2013.01); *A61B 17/3415* (2013.01); *A61B 17/3468* (2013.01); *A61B 2017/00575* (2013.01); *A61B 2017/00592* (2013.01); *A61B 2017/00606* (2013.01); *A61B 2017/00623* (2013.01);

(Continued)

(58) Field of Classification Search
CPC ..................... A61B 17/0057; A61B 17/12172; A61B 17/3415; A61B 2017/00575; A61B 17/12109; A61B 17/3439; A61B 17/3468; A61B 2017/00592; A61B 2017/00606; A61B 2017/00867; A61B 2017/00623; A61F 2/95; A61F 2/962; A61F 2/966; A61F 2002/9665; A61F 2/97
USPC .......................... 623/1.11, 1.23; 606/108, 213
See application file for complete search history.

(56) References Cited

U.S. PATENT DOCUMENTS

| 4,665,918 A * | 5/1987 | Garza et al. ................... 606/108 |
| 5,320,639 A | 6/1994 | Rudnick |

(Continued)

FOREIGN PATENT DOCUMENTS

WO        02/19926      3/2002

*Primary Examiner* — Jing Ou
(74) *Attorney, Agent, or Firm* — The Farrell Law Firm, P.C.

(57) ABSTRACT

A device for placing a vascular implant including a device for dilating a vessel, has an outer envelope and a tapered end piece for introduction into a vessel. The end piece includes a nose formed at the distal extremity of the outer envelope. The dilation device includes elements for opening the nose having at least two longitudinal slots which divide the nose into several segments which can be opened out in order to open the nose; and an implant which is placed in the outer envelope. The implant includes an expandable element which can be placed in the outer envelope. The implant includes an expandable element which can be placed on the internal wall of the outer envelope and is provided with elements for the translation of the implant in relation to the outer envelope such that the expandable element can press against the internal wall of the nose in order to open out the segments. A device for placing vascular implants fitted with the device is also disclosed.

3 Claims, 4 Drawing Sheets

(51) Int. Cl.
*A61B 17/12* (2006.01)
*A61F 2/966* (2013.01)
*A61F 2/95* (2013.01)
*A61F 2/962* (2013.01)
*A61B 17/00* (2006.01)
*A61B 17/34* (2006.01)

(52) U.S. Cl.
CPC ............... *A61B 2017/00867* (2013.01); *A61B 2017/1205* (2013.01); *A61F 2002/9665* (2013.01)

(56) References Cited

U.S. PATENT DOCUMENTS

| | | | |
|---|---|---|---|
| 5,433,723 A * | 7/1995 | Lindenberg et al. | 606/198 |
| 5,593,412 A * | 1/1997 | Martinez et al. | 623/1.11 |
| 5,634,928 A * | 6/1997 | Fischell et al. | 623/1.11 |
| 5,938,696 A * | 8/1999 | Goicoechea et al. | 606/194 |
| 6,030,364 A | 2/2000 | Durgin et al. | |
| 6,391,036 B1 | 5/2002 | Peterson et al. | |
| 6,596,011 B2 * | 7/2003 | Johnson et al. | 606/200 |
| 2002/0042622 A1 | 4/2002 | Donohoe et al. | |
| 2002/0107482 A1 | 8/2002 | Osypka et al. | |

* cited by examiner

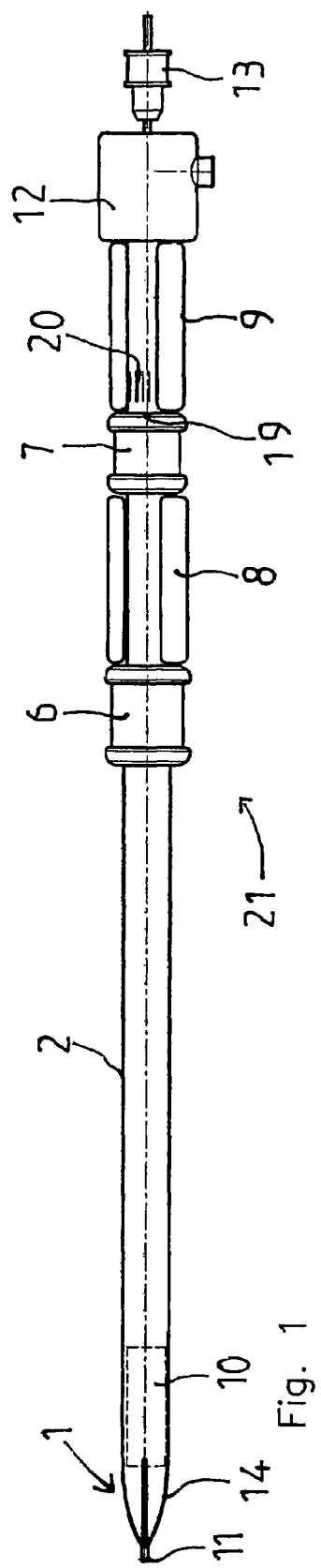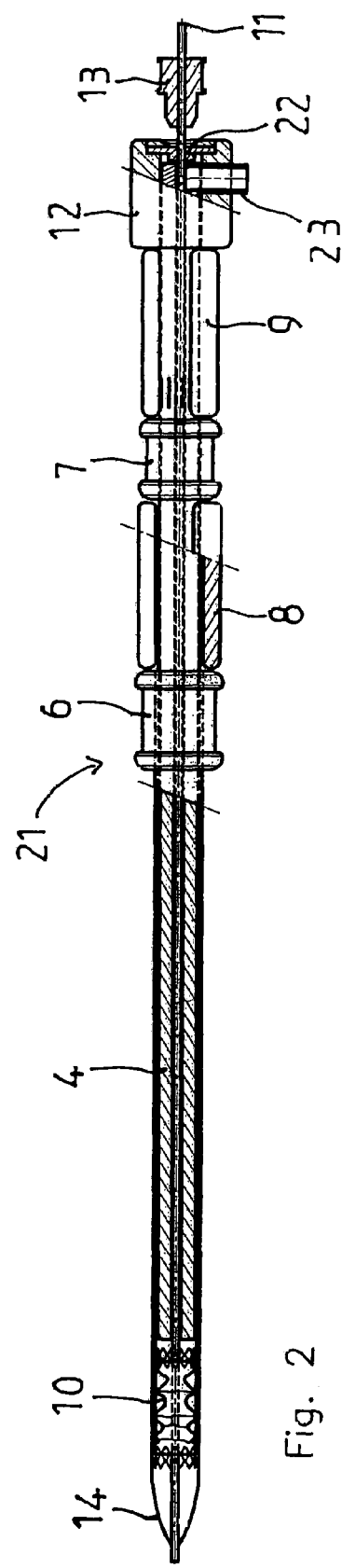

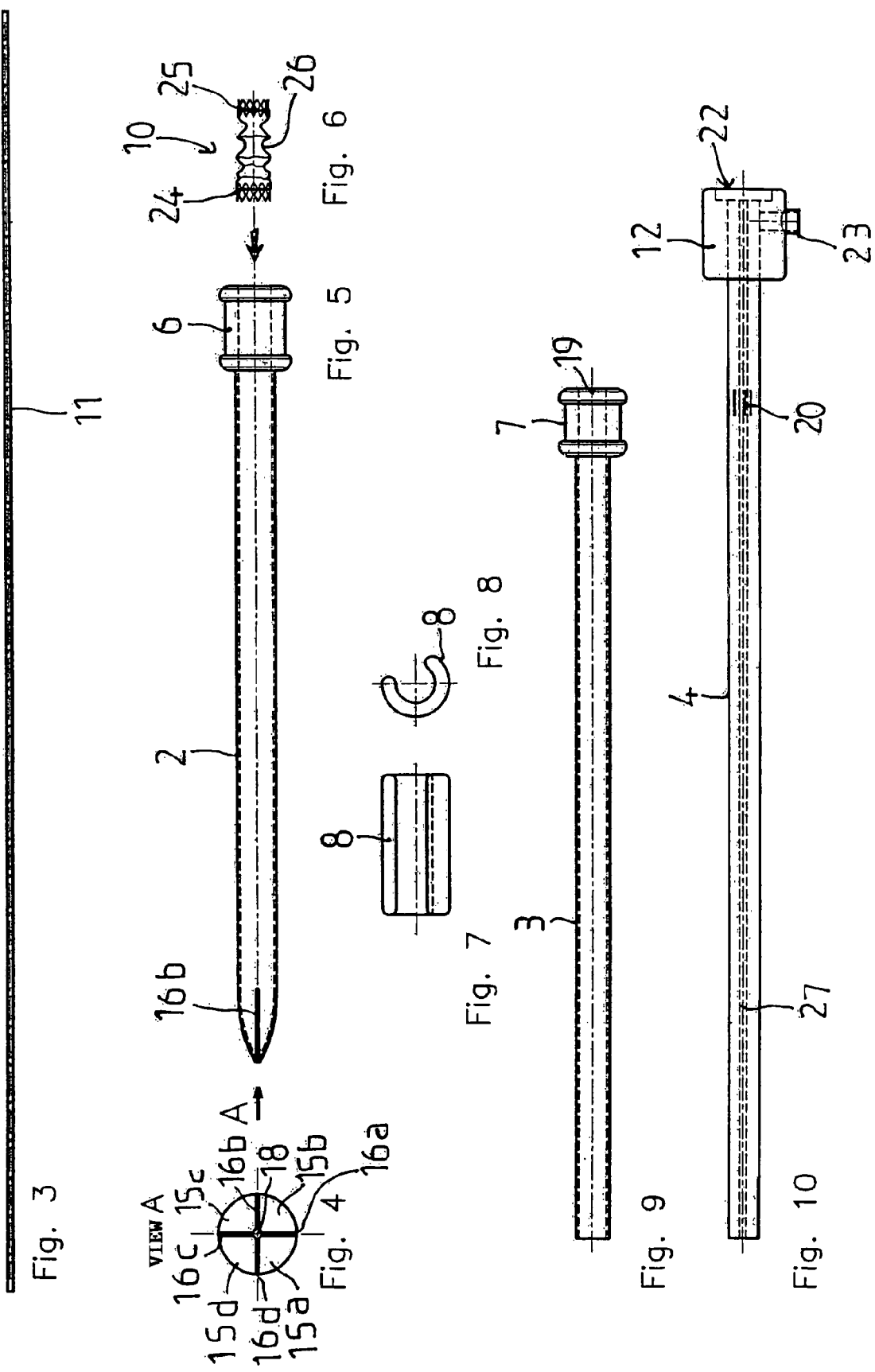

DEVICE FOR PLACING A VASCULAR IMPLANT

This invention relates to a device for placing a vascular implant.

It will be particularly useful for the use of catheters or any other instrument used to place an implant in a vessel in a human or animal body.

The invention may be used to place, in a vessel, devices such as stents or vaso-occlusive devices as described, for example, in document WO-A 02 19 926 or "coil" type implants.

The invention may also be used to place trans-parietal occlusive devices to block an opening in a vessel. This being so, the term "implant" is taken here in its widest possible sense.

The placing of implants in a vessel requires a trans-parietal opening (formed by penetrating the various layers of tissue) in order to reach the internal lumen of the said vessel.

In most cases, a dilation instrument is used for this purpose. It comprises a tapered end used to gradually increase the diameter of the passage through the vascular wall.

In most cases, a needle is inserted through the vascular wall and a guide is inserted, generally in the form of a guide wire with an end piece maintained in position in the lumen. Other instruments are threaded onto the guide wire and guided through the opening in the vascular wall. These instruments usually consist of an introductory instrument with a centrally tapered end to gradually increase the diameter of the parietal opening. The centrally tapered element is surrounded by an outer envelope which is eventually introduced through the parietal wall once the centrally tapered section has produced the necessary opening. The tapered element can then be withdrawn and the external envelope is maintained in position and used for the purposes of the required surgical procedure.

It is, for example, the residual outer envelope which is used to place a vascular implant. During these phases of the procedure, the guide wire can remain in place.

The usual technique, as described above, has a large number of disadvantages.

Firstly, the tapered section used for the gradual introduction of instruments lies in an internal part of the device until it reaches the diameter of the outer envelope. This being so, the internal tapered section obstructs the interior of the outer envelope during one whole phase of the procedure, and this precludes, in particular, any possibility of another functional or implantable element (e.g. a vascular implant) being present within the outer envelope until the introduction procedure has been completed.

Another disadvantage of current introducers is the area of dimensional transition between the internal tapered element and the outer wall of the outer envelope. This creates a break in diameter, which may be prejudicial to the continuity of movement when undertaking the introduction procedure and may damage the internal wall of the vessels.

Said document WO-A-02 19 926 refers to a vaso-occlusive device consisting of two expandable elements used to fix it in place by pressing against two sections of the wall of the vessel. It also includes an intermediate section that can be deformed by twisting, with the degree of deformation depending on the relative position of the two expandable elements, creating an area of maximum stricture that defines the degree of occlusion. Said document also describes a procedure for use and a device for the placing of this occlusive device.

The dilation instruments known at the present time are inappropriate for techniques of the type described in WO-A-02 19 926, in particular because they exclude the presence of a functional element in the interior until the end of introduction into the vessel.

US-A1-2002 0042622 describes a medical device for anastomosis procedures. This device includes a trochar used to transfix the wall of a vessel. The trochar, which has a tapered, opening end piece, nevertheless has a very limited function according to this prior disclosure since it is used solely for perforation purposes.

The present invention overcomes the disadvantages of the devices known at present. It allows for gradual introduction, an increase in the diameter of the parietal opening and centring within a vessel using a single external device which is also used to release the implant.

The present invention does not require the interior of the device to be blocked because there is no tapered central section to remove.

The interior of the device therefore remains empty, allowing in particular for the placing of an implant in the device at the beginning of the procedure. It is possible, for example, to sell an instrument fully equipped with the required implant.

Moreover, it is possible to perform several procedures within the vessel during the same surgical operation. Thanks to a shape-memory system, the invention can perform an initial introduction, be closed until it reaches another vascular section and be used there a second time.

The invention characteristically includes an envelope containing the dilation device which both dilates and contains the implant directly applied, at least partially, against the internal wall. This produces a compact device (fewer layers of envelopes) which makes positioning easier. It can also be guided by a traditional central guide wire.

The envelope is, therefore, also used as a centring device within the vessel. Moreover, one area in the centre of the device is left free, leaving room to pass a dilation balloon through it, for example.

It should also be noted that the implant is totally protected during positioning. When an expandable device is released, the tapered nose of the envelope ensures that release is gradual, avoiding the "jump" that is usually caused by the sudden variation in the diameter of a stent when released from the placing device.

Further aims and advantages will become apparent during the following description of a method of procedure which, though preferred, is not restrictive.

This invention relates to a device for the placing of a vascular implant including the following:
- a vessel dilation device with an outer envelope and a tapered end piece for introduction into the vessel whereby said end piece consists of a nose formed at the distal extremity of the outer envelope and the dilation device comprises means for opening the nose consisting of at least two longitudinal slots which divide the nose into several segments which can be opened out in order to open the nose;
- an implant placed in the outer envelope characterised in that:
  - the implant comprises an expandable element which can be placed on the internal wall of the outer envelope
  - it is provided with means for the translation of said implant in relation to the outer envelope such that the expandable element can press against the internal wall of the nose in order to open out the segments.

The device can also be characterised by the following advantageous but not restrictive variations:
- the means of translation include an inner sheath assembled in such a way as to slide along inside the outer envelope and push the expandable element
- the implant includes a second, hollow expandable element and an intermediate section that is hollow and deformable by twisting
- the second expandable element pushes against the internal wall of the inner sheath
- the inner sheath is assembled to slide and rotate within the outer envelope
- it includes a grip that is an integral part of the outer envelope
- it includes a grip that is an integral part of the inner sheath
- the grip on the inner sheath is located behind the grip on the outer envelope and includes a removable spacer placed between the two grips to keep them apart
- the unfolding elements are joined along the length of the slots when the nose is closed
- it includes a slot-type connection between the slots
- the nose includes a residual central passage
- the nose includes a shape memory so that it is closed by default when the opening elements are not active
- it includes a plunger that slides along the inner sheath and can be pushed against the free end piece of the second expandable element
- it includes a grip that is an integral part of the plunger located behind a grip on the inner sheath and a removable spacer located between said grips to keep them apart
- it includes the means of adjusting the angle of the inner sheath
- it includes a central channel along the line of the outer envelope to allow for the insertion of a guide wire

BRIEF DESCRIPTION OF THE DRAWINGS

The enclosed drawings are for information only and do not restrict the invention. They represent only one means of producing the invention and are designed to aid understanding.

FIG. 1 is a general side view of a positioning device according to the invention.

FIG. 2 is a cross-section.

FIG. 3 is one example of a guide wire.

FIG. 5 is a side view of an outer envelope and FIG. 4 is a front view of said envelope.

FIG. 6 illustrates a possible, but not restrictive, configuration of an implantable device for vascular occlusion.

FIGS. 7 and 8 illustrate respectively side and front views of a spacer that can be used in the positioning device described in the invention.

FIG. 9 is a side view of an inner sheath that can be used according to the invention and FIG. 10 is a side view of a plunger.

In this respect, FIG. 11 is a partial cross-section of the dilation device fitted with an implant.

FIG. 12 shows one stage in the modification of the configuration of the device, with the removal of a spacer.

FIG. 13 shows a partial side view of the invention, showing one example of a tapered nose on the outer envelope.

FIG. 14 shows the relative movement of various elements in the invention device used to open the nose.

FIG. 15 shows another phase in the working of the positioning device according to the invention.

FIG. 16 is a close-up view.

FIG. 17 shows a final phase in the use of the instrument with the removal of a second spacer.

FIG. 18 is a close-up view.

DETAILED DESCRIPTION OF THE INVENTION

Figure 11:
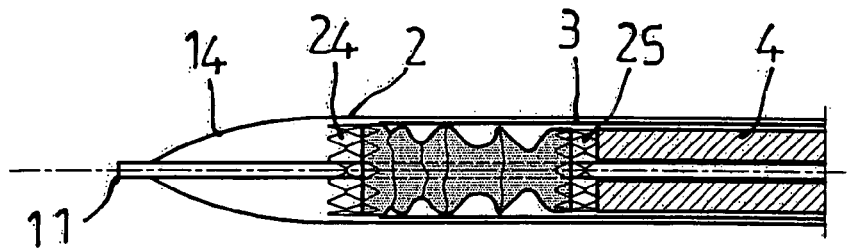
FIGS. 11 to 18 illustrate, in chronological order, various phases in the use of the implant positioning device according to the invention.

The term "dilation" as used in the invention refers to:
- the dilation of a narrowed area by a solid instrument of progressively increasing size. The tapered end piece widens the opening by gradually forcing the walls apart or, by extension, forcing apart the tissues in the area of penetration. The profile of the dilator also ensures that the instrument is centred automatically. This type of profile limits the risk of producing a lesion on the inner walls of vessels, often covered with calcified plaques;
- use for "therapeutic" dilation as performed by inflating a balloon and using endoprosthesis. The pressure exerted on the walls breaks up the calcified plaques and, it is hoped, will leave the vessel dilated once the balloon is deflated. An incomplete result is improved by the placing of an endoprosthesis.

WO-A 02 19 926 refers to a specific vaso-occlusive device including two expandable elements at the tip and an intermediate section that is deformable by twisting, thereby modifying the relative angle of the two expandable elements at the end piece.

The following description details the use of the device according to the invention when placing the vaso-occlusive device indicated in said document. However, this is merely one example of a possible use and should not be considered as a limitation on the application of the present invention. In particular, the device may be used to place other types of implant, especially with a single element expandable across its width. The expandable element may be auto-expandable or expandable by means of a balloon.

FIGS. 1 and 2 show a side view and cross-section of a positioning device according to the invention. This device (21) includes, in its front section, a vessel dilation device (1). Unlike the dilation device (1), the positioning device (21) has a section enabling the practitioner to handle it. In particular, grips (6), (7) and (12) are designed to be hand-held. Grip (12) can include or receive a range of different accessories such as a valve (22) to maintain the seal of the instrument and a connector (23) used for the connection of additional lines.

There follows a more detailed description of the various components of the dilation device (1) and positioning device (21) according to the invention as shown in the illustrated embodiment.

In this respect, FIG. 3 shows the formation of a guide wire (11) which can be positioned and maintained in the central section of device (1) and positioning device (21) during all phases of use of the invention.

FIGS. 4 and 5 show an outer envelope (2) constituting the main body of the device and limiting an interior area of work. The outer envelope includes a distal end piece consisting of a tapered nose (14) configured to allow for insertion into a vessel through the wall of said vessel.

During use, the nose (14) is initially in the default closed position, forming the tapered insertion profile. When the nose (14) has been inserted sufficiently into the vessel, the means are provided whereby the nose (14) can be opened.

There follows one example of these means of opening. In the case of FIGS. 4 and 5, the nose (14) is equipped with several slots (16a, 16b, 16c and 16d) which divide the nose

(14) into several segments (15a, 15b, 15c and 15d). The segments (15a, 15b, 15c and 15d) have relative freedom of movement so that the nose (14) can be opened in a movement substantially similar to the opening of a flower's petals.

The number of slots (16a, 16b, 16c and 16d) on device (1) and their longitudinal length are not restricted to the example illustrated here.

As an added advantage, the segments (15a, 15b, 15c and 15d) of nose (14) have a shape memory and therefore return to their closed standby position when the opening means are no longer active. This means that the nose (14) can be opened and closed several times as required by the practitioner.

Other means can be used to close the nose (14), for example an active closure system whereby a wire is threaded through the various segments (15a, 15b, 15c and 15d) between the end piece of the nose (14) and a peripheral grip. The tension of the wire closes the nose (14) and its release can also be used to open the nose (14).

At the opposite end of the outer envelope (2), there is a grip (6) for use by the practitioner. It should be noted that the outer envelope (2) creates an inner space allowing, for example, for the insertion of a vaso-occlusive device (10) presented in FIG. 10 and including two expandable elements (24) and (25) and a flexible intermediate section that is deformable by twisting (26).

Device (1) and the positioning device (21) also include an inner sheath (3) which can be mounted in such a way as to slide in the internal area of the outer envelope (2). Like the outer envelope (2), the inner sheath (3) can consist of a substantially cylindrical element with a circular cross-section. The distal end piece of the inner sheath is left free while the other end piece includes a grip (7) enabling the device to be held by the practitioner.

The invention also includes a plunger (4) visible in FIG. 10 in the preferred embodiment of the invention, wherein it is possible to include a central channel (27) in this plunger to create a residual passage in the heart of the device. There is also a grip (12) which, in the example shown, includes an end valve (22) and a connector (23) for the connection of accessories. Plunger (4) is mounted in such a way as to slide in the inner area of inner sheath (3).

This assembly produces the configuration illustrated in FIGS. 1 and 2. Grips (6), (7) and (12) are kept apart by removable spacers (8) and (9) which can be successively removed during the surgical procedure.

In this example the guide wire (11) is positioned in the residual central channel (27) of plunger (4) and its proximal end is linked to a sleeve which is also used when handling the device.

Figure 14:
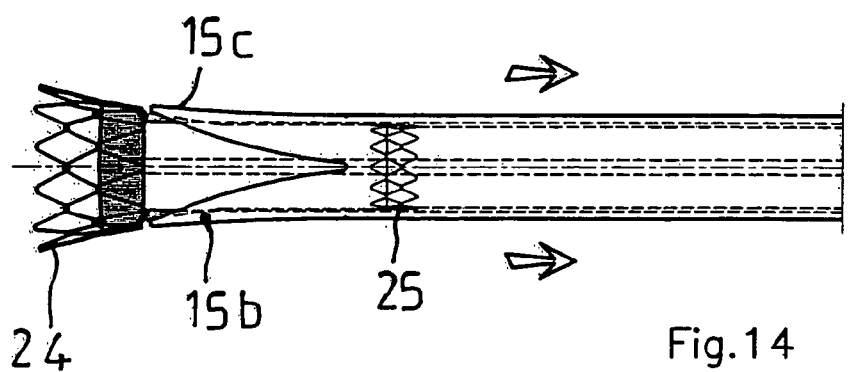
Figure 15:
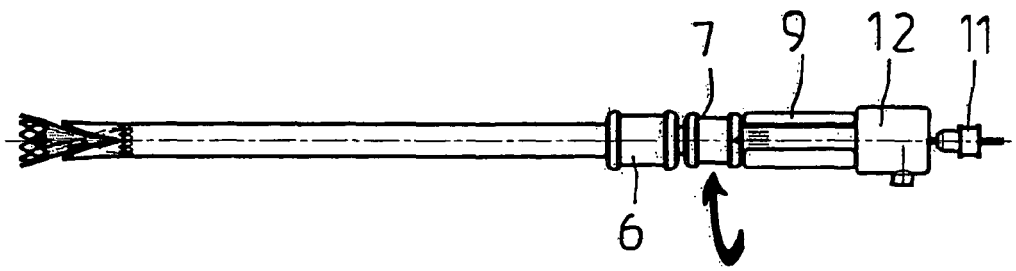

In the example shown, the nose (14) is opened as follows. From a closed position illustrated, for example, in FIG. 11, the practitioner removes the first spacer (8) to allow the removal of the outer envelope (2) from the inner sheath (3) until grips (6) and (7) reach the stop. During this withdrawal process, the distal end piece of the inner sheath (3) presses against the inner wall of outer envelope (2) by means of an expandable element (24) on the implant (10). This compression causes the deployment of segments (15a, 15b, 15c and 15d) of the nose (14) as shown in FIG. 14.

According to one possibility, temporary connections (17) are present along slots (16a, 16b, 16c and 16d) in order to maintain the pre-defined cohesion between the various segments (15a, 15b, 15c and 15d) during the introduction phase. The connections (17) are designed not to hinder the deployment of the nose (14) and to allow for the detachment of the various segments (15a, 15b, 15c and 15d) by means of the compression exercised by the inner sheath (3) during withdrawal from the outer envelope (2).

Temporary soldering can be used as connections (17).

There follows a more detailed description of one example of an implant positioning device, this being a non-restrictive example of the positioning of vaso-occlusive implants as shown in FIG. 6.

In this case, the implant (10) is positioned within the outer envelope (2) before the start of the operation. More precisely, the expandable distal element (24) is maintained by the inner wall of the outer envelope (2). Behind it is the other expandable element (25), maintained in position against the inner wall of the inner sheath (3). Advantageously, the rear end piece of the expandable element (24) is pressed against the front end piece of the inner sheath (3). At the same time, the rear end piece of the expandable element (25) is pressed against the distal end piece of the plunger (4). This configuration is well illustrated in FIG. 11.

Figure 12:
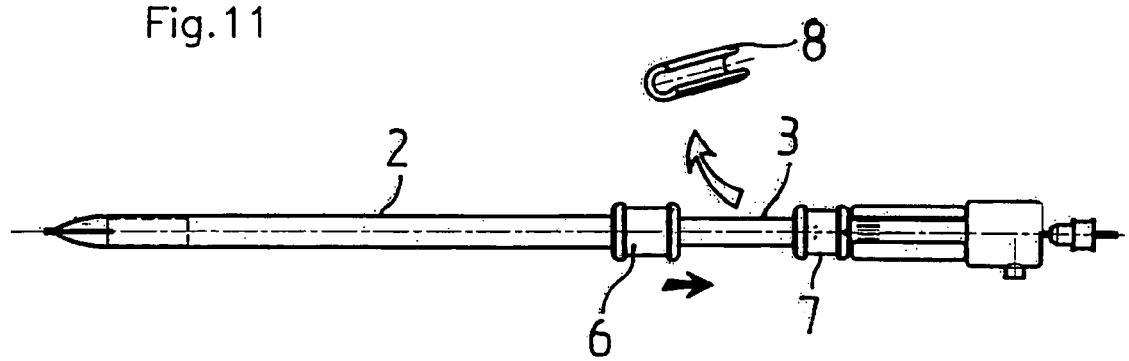
Figure 13:
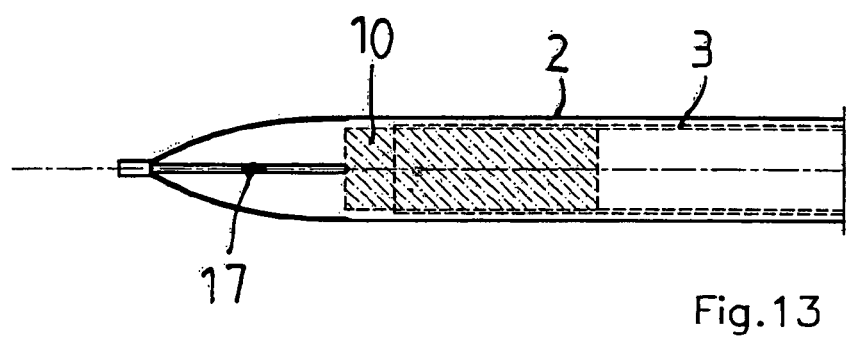

Initially, the practitioner inserts the nose (14) through the vascular wall until it reaches the required position for the implant. At this point, the spacer (8) is removed, enabling the practitioner to withdraw the outer envelope (2) from the inner sheath (3) using grip (6). This movement is illustrated in FIG. 12. It causes the expandable element (24) and the inner sheath (3) to press against the inner wall of the outer envelope (2), thereby deploying the nose (14) by pushing apart the various segments (15a, 15b, 15c and 15d). This situation is illustrated in FIG. 14 where the expansion of the expandable element (24) after release is clearly seen.

At this stage, the other expandable element (25) is still maintained inside the inner sheath (3).

Figure 16:
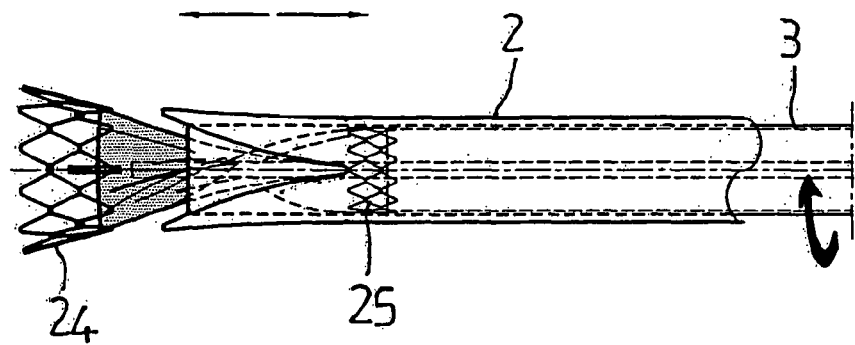
Figure 17:
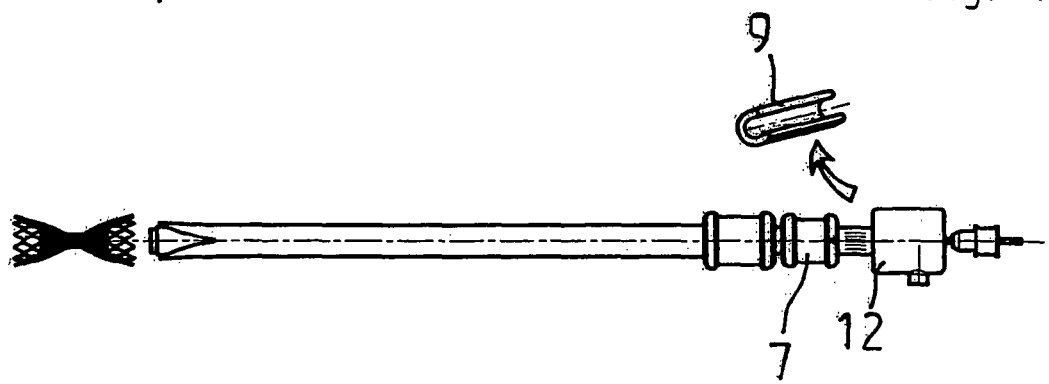

During vascular occlusion procedures, it is then possible to rotate the inner sheath (3) so as to modify the relative angle of the expandable elements (24) and (25). To do this, the practitioner uses the grip (7) and modifies the angle. It goes without saying that, in this application, the inner sheath (3) must be able to rotate along the longitudinal axis of the device. Moreover, it is advantageous to allow for the means of adjusting the angle of the inner sheath (3), for example through a marker (19) situated on the grip (7), one of a series of gradations (20) on the outer surface of the plunger (4) in a position that is visible to the user. The user can then adjust the amount of twist of the intermediate section (26) in order to adjust the degree of occlusion. The length of the implant (10) can be varied by carrying out a smaller or larger number of rotations. This possibility is illustrated in FIG. 16 by the double arrow.

By removing the spacer (9), the practitioner can remove the entire device consisting of the outer envelope (2) and the inner sheath (3), moving it backwards by moving grip (7) closer to grip (12) until it reaches the stop.

Figure 18:
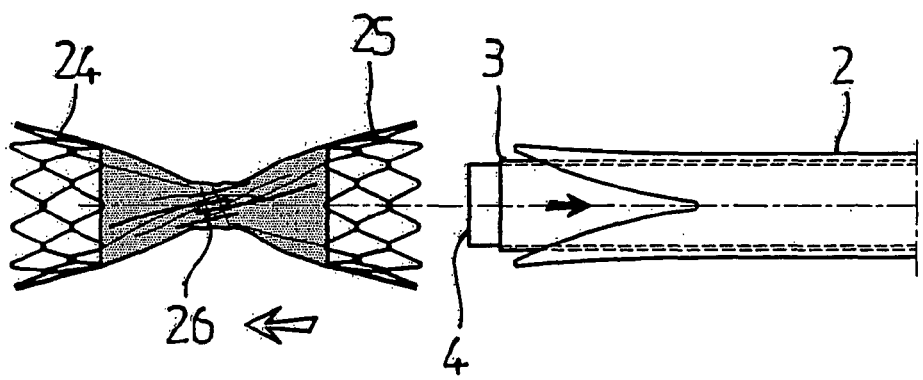

At this stage, the pressure exercised by the plunger (4) on the rear end piece of expandable element (25) releases said expandable element (25) from the inner wall of the inner sheath (3), causing the element (25) to expand and positioning it on the vascular wall. This is the situation illustrated in detail in FIG. 18 in which the nose (14) is behind the inner sheath (3), itself behind the plunger (4). It goes without saying that, here, the positions of relative withdrawal are accentuated to aid understanding.

The guide wire (11) may be withdrawn at this point or could have been withdrawn previously. Note that the nose (14) includes a central residual passage (14) which is visible on the front view in FIG. 4. It allows for the insertion and withdrawal of the guide wire (11).

The spacers (8) and (9) consist here of elements with a crescent-shaped cross-section angled at more than 180°. The remaining opening makes it possible to make use of the elasticity of the spacer material in order to remove it. One example of the shape of spacers (8) and (9) is presented, in the case of the spacer (8), in FIGS. 7 and 8. It goes without saying that another configuration is possible with other means used to remove the spacer.

The main components of the invention are made of polyurethane or polyethylene, for example.

REFERENCES

1. Vessel dilation device
2. Envelope
3. Inner sheath
4. Plunger
6. Envelope grip
7. Sheath grip
8. Spacer
9. Spacer
10. Implant
11. Guide wire
12. Plunger grip
14. Nose
15*a*, 15*b*, 15*c*, 15*d*. Segments
16*a*, 16*b*, 16*c*, 16*d*. Slots
17. Temporary connector
18. Residual passage
19. Marker
20. Gradation
21. Positioning device
22. Valve
23. Connection
24. Expandable element
25. Expandable element
26. Intermediate section
27. Central channel

The invention claimed is:

1. A method for placing an implant, the method comprising:
    housing the implant within an envelope of an implant placement device, wherein the implant includes an auto-expandable element that expands in a radial direction perpendicular to a longitudinal axis of the device, wherein the device includes a plunger, a sheath for confining a portion of the implant to restrict expansion of the auto-expandable element, and a nose positioned at a distal end of the envelope having a plurality of slots configured to divide the nose into a plurality of outwardly opening segments;
    moving, with the implant contained within the sheath between the plunger and the nose, the implant placement device to a desired position for placement of the implant;
    removing a spacer and sliding the envelope disposed around the sheath in a proximal direction to cause the auto expandable element to contact an interior of the plurality of outerly opening segments, thereby opening the nose; and
    moving the plunger in a longitudinal direction within the sheath to discharge the implant from the device.

2. The method of claim 1, wherein the nose includes a shape memory that closes the nose as a default position.

3. The method of claim 1, further comprising:
    moving a first grip to slide the envelope on the sheath; and
    moving the first grip in the proximal direction towards a second grip to expose a front end of the auto-expandable element of the implant.

\* \* \* \* \*